United States Patent
Booth et al.

(10) Patent No.: US 8,805,592 B1
(45) Date of Patent: Aug. 12, 2014

(54) FLUID IDENTIFICATION AND TRACKING

(75) Inventors: Donald W Booth, Charleston, WV (US); Tony Anderson, Charleston, WV (US)

(73) Assignee: Cascades Coal Sales, Inc., Charleston, WV (US)

(*) Notice: Subject to any disclaimer, the term of this patent is extended or adjusted under 35 U.S.C. 154(b) by 323 days.

(21) Appl. No.: 13/044,610

(22) Filed: Mar. 10, 2011

Related U.S. Application Data (60) Provisional application No. 61/312,721, filed on Mar. 11, 2010.

(51) Int. Cl.
G05D 11/00 (2006.01)
B67D 7/32 (2010.01)
B67D 7/34 (2010.01)
G01N 33/00 (2006.01)

(52) U.S. Cl.
CPC ............ *B67D 7/3209* (2013.01); *B67D 7/346* (2013.01); *G01N 33/0004* (2013.01)
USPC .............. 700/283; 141/94; 141/95; 141/2; 340/521; 701/31.4; 701/32.3; 700/281

(58) Field of Classification Search
USPC ......... 700/283, 282; 239/172; 141/1, 23, 95, 141/122, 231, 2, 94; 340/521, 539.11; 701/31.4, 482, 32.3
See application file for complete search history.

(56) References Cited

U.S. PATENT DOCUMENTS

| | | | | |
|---|---|---|---|---|
| 4,072,934 A * | 2/1978 | Hiller et al. | | 340/608 |
| 4,166,483 A * | 9/1979 | Nordlund | | 141/1 |
| 4,345,146 A * | 8/1982 | Story et al. | | 235/381 |
| 4,598,742 A * | 7/1986 | Taylor | | 141/95 |
| 5,091,716 A * | 2/1992 | Nelson et al. | | 340/605 |
| 5,091,863 A * | 2/1992 | Hungerford et al. | | 700/283 |
| 5,259,424 A * | 11/1993 | Miller et al. | | 141/4 |
| 5,737,227 A * | 4/1998 | Greenfield et al. | | 705/400 |
| 5,983,962 A * | 11/1999 | Gerardot | | 141/231 |
| 6,042,258 A * | 3/2000 | Hines et al. | | 366/8 |
| 6,042,259 A * | 3/2000 | Hines et al. | | 366/17 |
| 6,082,888 A * | 7/2000 | Sakayori | | 700/283 |
| 6,148,291 A * | 11/2000 | Radican | | 705/28 |
| 6,481,627 B1 * | 11/2002 | Guerreri | | 235/472.01 |
| 6,496,775 B2 * | 12/2002 | McDonald et al. | | 701/469 |
| 6,611,755 B1 * | 8/2003 | Coffee et al. | | 701/482 |
| 6,779,568 B2 * | 8/2004 | Borck | | 141/67 |
| 6,892,131 B2 * | 5/2005 | Coffee et al. | | 701/482 |
| 6,931,305 B2 * | 8/2005 | Sherwood | | 700/282 |

(Continued)

OTHER PUBLICATIONS

S & A Systems, Inc., "Welcome to the Fleetwatch® Fluid Management System Products Page", 2008, Retrieved from the Internet at "www.fleetwatch.com/products.php".*

*Primary Examiner* — Mohammad Ali
*Assistant Examiner* — Kelvin Booker
(74) *Attorney, Agent, or Firm* — Dinsmore & Shohl LLP; Monika J. Hussell, Esq.

(57) ABSTRACT

Embodiments disclosed herein include systems and methods for fluid identification and tracking. At least one embodiment of a method includes determining that a vehicle is discharging a fluid, determining an ingredient of the fluid, and determining a first vehicle location. Some embodiments include determining, based on the ingredient, whether discharge of the fluid at the first vehicle location is allowable and in response to determining that discharge of the fluid at the first vehicle location is not allowable, performing, by a computing device, a first preventative measure.

14 Claims, 10 Drawing Sheets

(56) References Cited

U.S. PATENT DOCUMENTS

| | | | |
|---|---|---|---|
| 7,177,780 B2* | 2/2007 | Hillam et al. | 702/156 |
| 7,178,561 B2* | 2/2007 | Memmott et al. | 141/1 |
| 7,181,361 B2* | 2/2007 | Memmott et al. | 702/130 |
| 7,185,683 B2* | 3/2007 | Hillam et al. | 141/198 |
| 7,197,409 B2* | 3/2007 | Hillam et al. | 702/55 |
| 7,327,251 B2* | 2/2008 | Corbett, Jr. | 340/539.13 |
| 7,346,427 B2* | 3/2008 | Hillam et al. | 700/236 |
| 7,489,993 B2* | 2/2009 | Coffee et al. | 701/32.3 |
| 7,536,264 B2* | 5/2009 | Hillam et al. | 702/55 |
| 7,546,256 B2* | 6/2009 | Hillam et al. | 705/28 |
| 7,574,385 B2* | 8/2009 | Hillam et al. | 705/28 |
| 7,628,182 B2* | 12/2009 | Poulter et al. | 141/244 |
| 7,689,371 B2* | 3/2010 | Memmott et al. | 702/55 |
| 7,783,435 B2* | 8/2010 | Hillam et al. | 702/55 |
| 7,805,340 B2* | 9/2010 | Blakeslee et al. | 705/28 |
| 8,051,882 B2* | 11/2011 | Koeninger et al. | 141/95 |
| 8,227,258 B2* | 7/2012 | Chang et al. | 436/180 |
| 8,361,009 B2* | 1/2013 | Lee et al. | 604/29 |
| 2003/0183382 A1* | 10/2003 | Newman | 166/66 |
| 2004/0039504 A1* | 2/2004 | Coffee et al. | 701/35 |
| 2004/0045623 A1* | 3/2004 | Parker et al. | 141/1 |
| 2004/0163731 A1* | 8/2004 | Eichelberger et al. | 141/284 |
| 2005/0103400 A1* | 5/2005 | Eichelberger et al. | 141/231 |
| 2005/0139286 A1* | 6/2005 | Poulter et al. | 141/234 |
| 2005/0270158 A1* | 12/2005 | Corbett, Jr. | 340/572.1 |
| 2006/0142913 A1* | 6/2006 | Coffee et al. | 701/35 |
| 2006/0157142 A1* | 7/2006 | Hillam et al. | 141/198 |
| 2006/0157143 A1* | 7/2006 | Memmott et al. | 141/198 |
| 2006/0157144 A1* | 7/2006 | Hillam et al. | 141/198 |
| 2006/0157145 A1* | 7/2006 | Hillam et al. | 141/198 |
| 2006/0157146 A1* | 7/2006 | Hillam et al. | 141/198 |
| 2006/0157147 A1* | 7/2006 | Hillam et al. | 141/198 |
| 2006/0157148 A1* | 7/2006 | Hillam et al. | 141/198 |
| 2006/0157149 A1* | 7/2006 | Hillam et al. | 141/198 |
| 2006/0157150 A1* | 7/2006 | Blakeslee et al. | 141/198 |
| 2006/0157151 A1* | 7/2006 | Memmott et al. | 141/198 |
| 2006/0161374 A1* | 7/2006 | Hillam et al. | 702/130 |
| 2007/0106543 A1* | 5/2007 | Baughman et al. | 705/7 |
| 2007/0143062 A1* | 6/2007 | Memmott et al. | 702/136 |
| 2007/0143067 A1* | 6/2007 | Hillam et al. | 702/156 |
| 2007/0181083 A1* | 8/2007 | Fulton et al. | 123/3 |
| 2008/0138674 A1* | 6/2008 | Pez et al. | 429/17 |
| 2009/0012449 A1* | 1/2009 | Lee et al. | 604/29 |
| 2009/0070175 A1* | 3/2009 | Bauqhman et al. | 705/8 |
| 2009/0088924 A1* | 4/2009 | Coffee et al. | 701/33 |
| 2009/0299805 A1* | 12/2009 | Baughman et al. | 705/9 |
| 2009/0315729 A1* | 12/2009 | Inhoffer | 340/632 |
| 2010/0023170 A1* | 1/2010 | Sherwood | 700/282 |
| 2010/0089486 A1* | 4/2010 | Koeninger et al. | 141/2 |
| 2010/0154920 A1* | 6/2010 | Poeschl | 141/1 |
| 2010/0185334 A1* | 7/2010 | Trottier et al. | 700/281 |
| 2011/0040503 A1* | 2/2011 | Rogers et al. | 702/55 |
| 2011/0120589 A1* | 5/2011 | Evans | 141/1 |
| 2011/0130882 A1* | 6/2011 | Perez | 700/282 |
| 2011/0230822 A1* | 9/2011 | Lee et al. | 604/29 |
| 2012/0022768 A1* | 1/2012 | Johnson et al. | 701/103 |
| 2012/0044068 A1* | 2/2012 | Koeninger et al. | 340/539.11 |
| 2012/0241367 A1* | 9/2012 | Childers et al. | 210/233 |
| 2013/0029009 A1* | 1/2013 | Darling et al. | 426/59 |

* cited by examiner

C-FIT

| Vehicle Number | Location | Current Action | Contents | OK? | Control |
|---|---|---|---|---|---|
| 12345 | Cincinnati, Ohio | Driving | $H_2O, C_8H_{18}$ | | |
| 67890 | Atlanta, Georgia | Filling | $H_2O$ | | |
| 23456 | Charlotte, North Carolina | Releasing | $H_2O, C_8H_{18}$ | NO | Shut Down |
| 78901 | New York, New York | Releasing | $H_2O$ | | |
| 34567 | San Diego, California | Filling | HCl | NO | Shut Down |
| 89012 | Sandusky, Ohio | Filling | $H_2O$ | | |
| 45678 | Columbus, Georgia | Releasing | $H_2O$ | | |
| 90123 | Columbus, Ohio | Driving | $H_2O$ | | |
| 56789 | Lexington, Kentucky | Driving | $H_2O$ | | |
| 01234 | Charleston, West Virginia | Releasing | $H_2O, C_8H_{18}$ | NO | Shut Down |

FIG. 4

C-FIT

| Vehicle Number | Location | GLOBAL LOCATION | Update | Control |
|---|---|---|---|---|
| 12345 | Cincinnati, Ohio | Lat: 39° 6'; Long: -84° 80' | Current | |
| 67890 | Atlanta, Georgia | Lat: 33° 52'; Long: -84° 20' | Current | |
| 23456 | Charlotte, North Carolina | Lat: 35° 13'; Long: -80° 50' | Current | |
| 78901 | Chicago, Illinois | Lat: 41° 56'; Long: -87° 39' | Not | Request |
| 34567 | San Diego, California | Lat: 32° 45'; Long: -117° 12' | Current | |
| 89012 | Sandusky, Ohio | Lat: 41° 28'; Long: -82° 42' | Current | |
| 45678 | Columbus, Georgia | Lat: 32° 27'; Long: -84° 59' | Not | Request |
| 90123 | Columbus, Ohio | Lat: 39° 57'; Long: -82° 57' | Current | |
| 56789 | Lexington, Kentucky | Lat: 38° 1'; Long: -84° 29' | Current | |
| 01234 | Charleston, West Virginia | Lat: 38° 21'; Long: -81° 37' | Not | Request |

FIG. 5

C-FIT

Vehicle Number: 01234  Location: Charleston, WV; Lat: 38° 37'

| Time | Location | Action | OK? | Control |
|---|---|---|---|---|
| Mon 1/1/11 9:03AM | Charleston, WV | Releasing | NO | Shut Down |
| Mon 1/1/11 6:17AM | Charleston, WV | Driving | YES | None |
| Sun 12/31/10 8:36PM | Dayton, OH | Driving | YES | None |
| Sun 12/31/10 7:22AM | Chicago, IL | Filling | YES | None |
| Sat 12/30/10 11:46AM | Chicago, IL | None | YES | None |
| Sat 12/30/10 9:03AM | Chicago, IL | Releasing | YES | None |
| Mon 12/30/11 8:28AM | Chicago, IL | Driving | NO | None |
| Mon 12/30/11 6:17AM | Chicago, IL | Filling | NO | Shut Down |

- Protective Measures (632)
- Show Map (634)
- Change restricted areas (636)
- Show Contents Concentrations (638)

FLUID IDENTIFICATION AND TRACKING

CROSS REFERENCE

This application claims the benefit of U.S. Provisional Application No. 61/312,721, filed Mar. 11, 2010 and entitled "C-Fluid Identification and Tracking Process," which is hereby incorporated by reference in its entirety.

BACKGROUND

1. Field

The present disclosure generally relates to fluid identification and tracking and, more specifically, to embodiments of systems and methods for monitoring the receipt, travel, and release of fluid in a vehicle.

2. Technical Background

Many fluids are shipped across the country by a fluid hauler in a vehicle for unloading at a destination location. Traditionally, the recording and reporting of this fluid transportation has been manual. While the manual recording and reporting has been helpful, oftentimes, the actual densities and other properties of the transported fluids have not been tested or recorded. Accordingly, the ingredients of the fluid are often assumed. Similarly, in many traditional instances, fluid volumes have been supplied by manual invoices or delivery tickets by the contracted fluids hauler. Accordingly, errors can occur in terms of recording, reporting, and monitoring the travel of the fluid.

SUMMARY

Embodiments disclosed herein include systems and methods for fluid identification and tracking. At least one embodiment of a method includes determining that a vehicle is discharging a fluid, determining an ingredient of the fluid, and determining a first vehicle location. Some embodiments include determining, based on the ingredient, whether discharge of the fluid at the first vehicle location is allowable and in response to determining that discharge of the fluid at the first vehicle location is not allowable, performing, by a computing device, a first preventative measure.

Similarly, embodiments include a non-transitory computer-readable medium for fluid identification and tracking that include a program that, when executed by a computing device, causes the computing device to determine that a vehicle is receiving a fluid, determine a ingredient of the fluid, and determine a first vehicle location. In some embodiments, the program causes the computing device to determine, based on the ingredient, whether receipt of the fluid at the first vehicle location is allowable and, in response to determining that receipt of the fluid at the first vehicle location is not allowable, perform a first preventative measure.

Further embodiments include a system for fluid identification and tracking that include a computing device that includes a memory component that stores logic that causes the computing device to determine that a vehicle is discharging a fluid, determine an ingredient of the fluid, and determine a first vehicle location. In some embodiments, the logic causes the computing device to determine, based on the ingredient, whether discharge of the fluid at the first vehicle location is allowable and in response to determining that discharge of the fluid at the first vehicle location is not allowable, perform a first preventative measure.

Additional features and advantages will be set forth in the detailed description which follows, and in part will be readily apparent to those skilled in the art from that description or recognized by practicing the embodiments described herein, including the detailed description which follows, the claims, as well as the appended drawings.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION

Embodiments disclosed herein include an automated recording and reporting process for transporting fluids and a process for determining density and fluid properties that can be measured by an electronic device for providing quality control and treatment. Similarly, some embodiments include tracking the movement of fluids loaded onto a vehicle. Tracking may be performed utilizing a computing infrastructure that includes global positioning hardware and/or software. The tracking may include determining at least one geographic location, time, date, fluid volume, fluid density, and direction of fluid flow through the vehicle (intake or discharge). In some embodiments, the vehicle may be tracked and traced from pickup to delivery of fluid on the internet via a satellite to several locations as desired. A user interface, such as a web interface, email, etc. may be provided to a user and/or administrator. These and other embodiments are disclosed in more detail below, with reference to the drawings.

Figure 1:
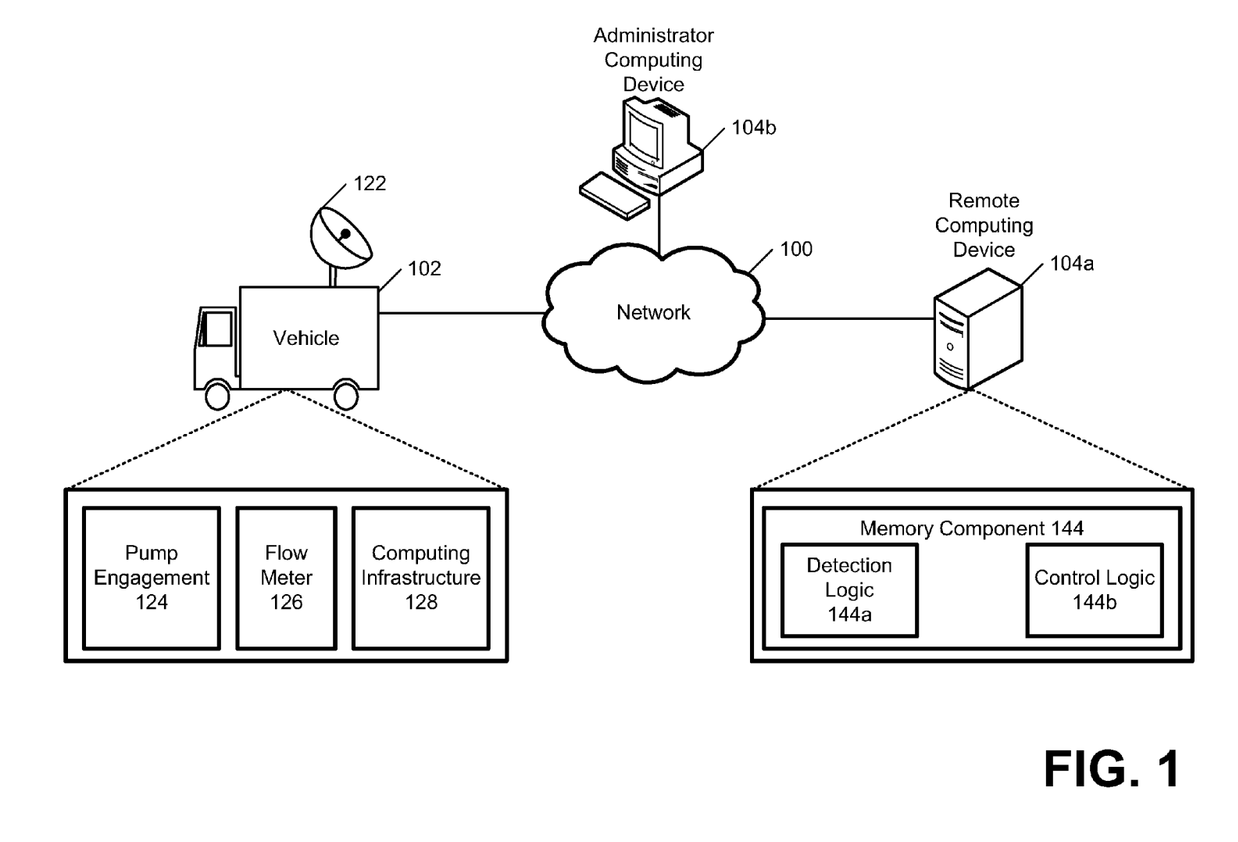
FIG. 1 depicts a computing environment for determining location and contents of a vehicle, according to embodiments disclosed herein.

Referring now to the drawings, FIG. 1 depicts a computing environment for determining location and contents of a vehicle, according to embodiments disclosed herein. As illustrated, a network 100 may be coupled to a vehicle 102, a remote computing device 104a, and an administrator computing device 104b. The network 100 may include a wide area network and/or a local area network and, thus may be wired and/or wireless. The vehicle 102 may include any type of car, truck, train, boat, plane, etc., that transports any type of fluid. Coupled to and/or part of the vehicle 102 is a receiving device 122, a pump engagement 124, a flow meter 126, and computing infrastructure 128. The receiving device 122 may be configured for receiving and/or transmitting data and may include a satellite receiver, global positioning receiver, wireless fidelity (Wi-Fi) receiver, cellular receiver, and/or other device configured for wireless communication. The pump engagement 124 includes any type of mechanism that facilitates the filling of the vehicle 102 with the fluid and/or discharging the fluid from the vehicle 102. The pump engagement 124 may utilize any mechanism for forcing the fluid into and/or out of the vehicle 102; however, in some embodiments, the mechanism may be a pumping mechanism. The pump engagement 124 may additionally include a flow start/stop mechanism for turning on and/or turning off intake or discharge of a fluid. Similarly, the flow meter 126 may include a micromotion coriolis meter and/or other device for measuring the flow and density of the fluid. Regardless of the particular device utilized, the flow meter 126 may be configured for determining a direction and rate of flow of a fluid into and/or out of the vehicle 102. From the measurements taken by the flow meter 126, the computing infrastructure 128, remote computing device 104a, and/or other computing device may determine various fluid properties of the fluid, including concentrations, ingredients, etc. The computing infrastructure 128 may include a programmable logic controller (PLC) and/or other computing device that is configured for controlling mechanical devices, such as the pump engagement 124 and flow meter 126. Additionally, similar to the computing structure shown in FIG. 2 and described below, the computing infrastructure 128 may also include an output device (such as a liquid crystal diode or other display), input devices, such as start buttons, stop buttons, keyboards, and/or other devices/components. The computing infrastructure 128 may also include a memory component that stores one or more pieces of logic for determining global position of the vehicle 102, determining contents of the fluid and/or determining flow of the fluid, as described in more detail with reference to FIG. 2, below.

Additionally, the remote computing device 104a may be coupled to the network 100 and may receive data from the vehicle 102. The remote computing device 104a includes a memory component 144, which stores detection logic 144a and control logic 144b. As described in more detail below, the detection logic 144a may facilitate determinations of vehicle location, fluid flow, and fluid contents. Similarly, the control logic 144b may be configured to facilitate performing remote control operations of the vehicle 102, based on information determined by the detection logic 144a. Additionally, the administrator computing device 104b may be configured for accessing data provided by the vehicle 102 and/or remote computing device 104a.

As described in more detail below, a vehicle driver may be instructed to pick up a predetermined amount of fluid from a first vehicle location. The computing infrastructure 128 and the receiving device 122 may provide global positioning information for directions, maps, etc. that help determine the location of and directions to the predetermined first location. Additionally, while in transit, the computing infrastructure 128 may determine whether the vehicle 102 is on a correct route to the predetermined first location. In some embodiments, this information may additionally be sent to the remote computing device 104a and/or to the administrator computing device 104b. Once the vehicle 102 has arrived at the predetermined first location, the computing infrastructure 128 may activate the pump engagement 124 for filling the vehicle 102 with the fluid. Additionally, the flow meter 126 may determine the amount of fluid that is entering the vehicle 102, as well as utilize a density analysis to determine the ingredients (e.g., a first ingredient, a second ingredient, etc.) and concentration of the fluid. If the ingredients and/or concentration are determined to be indicative of an improper fluid that is being filled into the vehicle 102, the computing infrastructure 128 may identify the improper filling and/or shut down a mechanism responsible for receiving and/or discharging fluid (such as the pump engagement 124). Similarly, in some embodiments, this functionality may be initiated by the remote computing device 104a.

Once the vehicle 102 has received the desired fluid, the vehicle 102 may travel to a predetermined second location and may be controlled and/or monitored, as discussed above. Upon determining that the vehicle has arrived at an appropriate destination for releasing the fluid, the computing infrastructure 128 may activate the pump engagement 124 to allow the release. If however, it is determined that the vehicle 102 enters a location that is not permitted for release of the determined fluid, the computing infrastructure 128 and/or the remote computing device 104a may prevent such release until the vehicle 102 reaches the predetermined second location and/or other approved location. Additionally, as described in more detail below, an email and/or web interface may be provided to the administrator computing device 104b for indicating the activities of the vehicle 102.

It should be understood that while the detection logic 144a and the control logic 144b are illustrated as residing on the remote computing device 104a, this is merely an example. In some embodiments, these logical components may instead (or additionally) reside on the computing infrastructure 128. As a consequence, in some embodiments, the vehicle 102 may perform the flow determination, vehicle location, fluid contents determination, vehicle control functions, etc. Similarly, while not expanded in FIG. 1, embodiments of the administrator computing device 104b may be equipped with similar logic for performing any of this functionality, as well.

It should also be understood that while the computing infrastructure 128, the remote computing device 104a, and the administrator computing device 104b are illustrated as a PLC, server, and personal computer, respectively, these are also merely examples. More specifically, depending on the particular embodiment, any similar computing hardware may be utilized to perform the described functionality.

Figure 3:
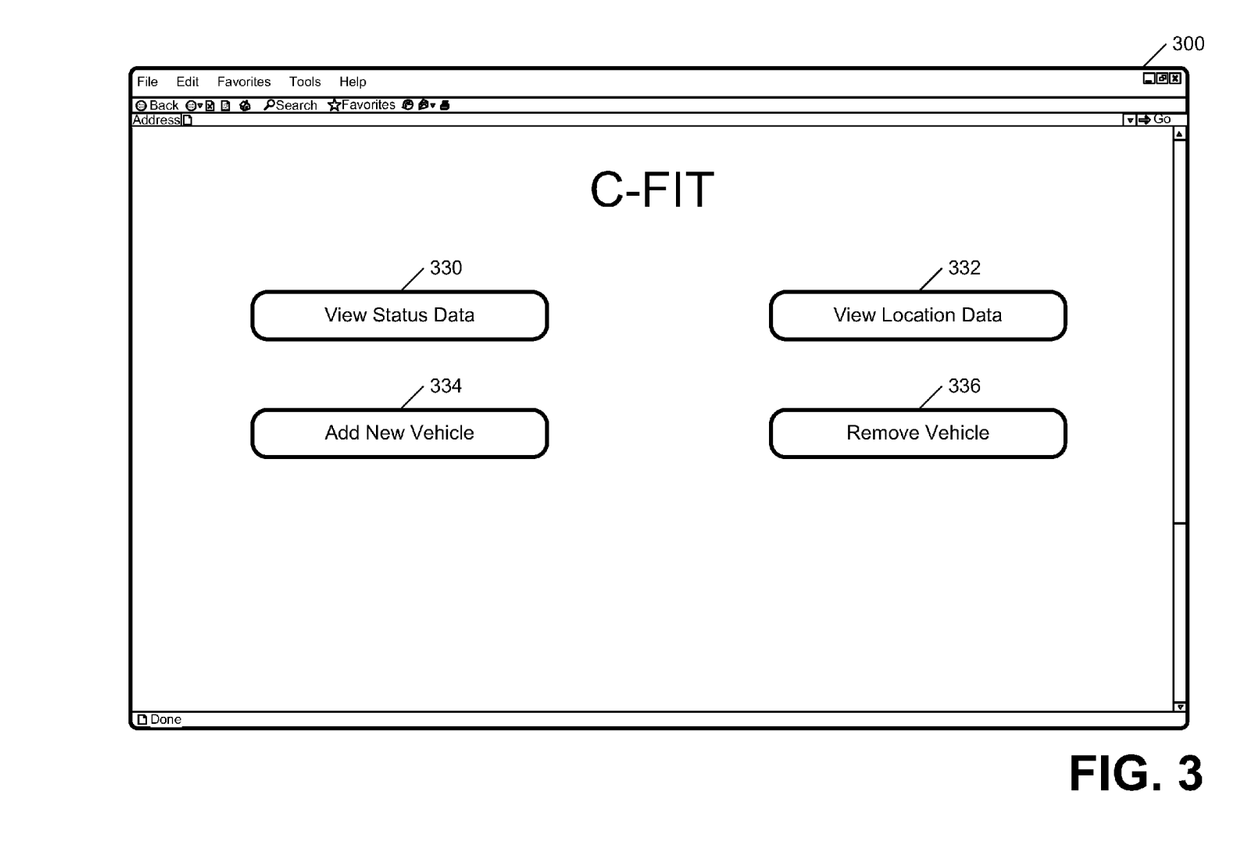
FIG. 3 depicts an interface for viewing data regarding a vehicle, according to embodiments disclosed herein.

Additionally, while not explicitly illustrated n FIG. 3, some embodiments may include one or more external databases and/or servers for providing information regarding allowable and restricted areas for different fluids. This information may be received from one or more different entities, including governmental agencies, private companies, etc. From this information, determinations can be made regarding whether the vehicle 102 is receiving and/or discharging fluid at an acceptable location.

Figure 2:
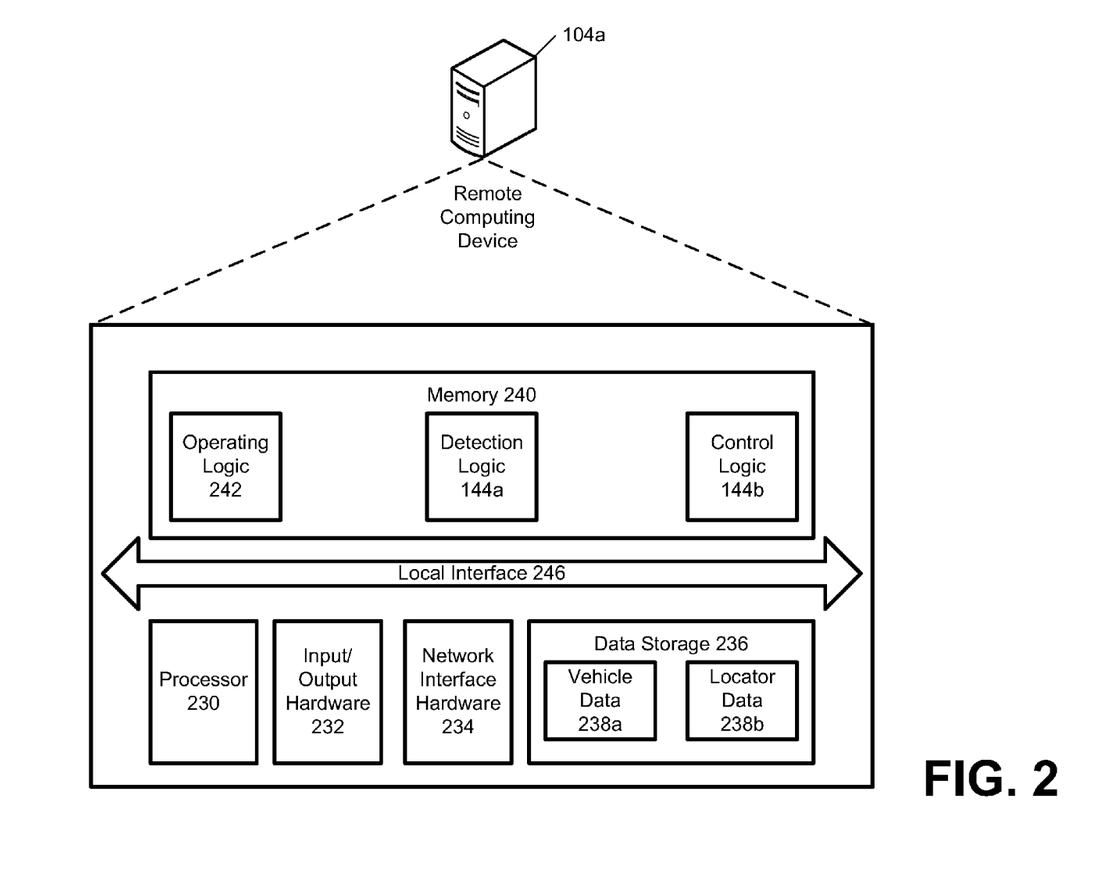
FIG. 2 depicts a computing architecture for determining the location and contents of a vehicle, according to embodiments disclosed herein.

FIG. 2 depicts a computing architecture for determining the location and contents of a vehicle 102, according to embodiments disclosed herein. In the illustrated embodiment, the remote computing device 104a includes a processor 230, input/output hardware 232, network interface hardware 234, a data storage component 236 (which stores vehicle data 238a, locator data 238b, historical data, and/or other data), and the memory component 144. The memory component 144 may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the remote computing device 104a and/or external to the remote computing device 104a.

Additionally, the memory component 144 may store operating logic 242, detection logic 144a, and the control logic 144b. The detection logic 144a and the control logic 144b may each include a plurality of different pieces of logic, each of which may be embodied as a computer program, firmware, and/or hardware, as an example. A local interface 246 is also included in FIG. 2 and may be implemented as a bus or other interface to facilitate communication among the components of the remote computing device 104a.

The processor 230 may include any processing component operable to receive and execute instructions (such as from the memory component 144 and/or the data storage 236). The input/output hardware 232 may include and/or be configured to interface with a monitor, positioning system, keyboard, mouse, printer, image capture device, microphone, speaker, gyroscope, compass, global positioning receiver, and/or other device for receiving, sending, and/or presenting data. The network interface hardware 234 may include and/or be configured for communicating with any wired or wireless networking hardware, including an antenna, a modem, LAN port, wireless fidelity (Wi-Fi) card, WiMax card, mobile communications hardware, satellite, and/or other hardware for communicating with other networks and/or devices. From this connection, communication may be facilitated between the remote computing device 104a and other computing devices.

The operating logic 242 may include an operating system and/or other software for managing components of the remote computing device 104a. Similarly, as discussed above, the detection logic 144a may reside in the memory component 144 and may be configured to cause the processor 230 to detect and/or monitor the position of the vehicle 102, the fluid receive and/or discharged by the vehicle 102, and report this data as an email, web interface, and/or other interface. Additionally, the control logic 144b may be configured to cause the processor 230 to control actions of the vehicle 102. As discussed above, in situations where the vehicle 102 is engaged in an activity that is deemed improper, the control logic 144b may cause the remote computing device 104a and/or the computing infrastructure 128 to shut down the improper operation (and/or take other preventative measure). Other functionality is also included and described in more detail, below.

It should be understood that the components illustrated in FIG. 2 are merely exemplary and are not intended to limit the scope of this disclosure. While the components in FIG. 2 are illustrated as residing within the remote computing device 104a, this is merely an example. In some embodiments, one or more of the components may reside external to the remote computing device 104a. It should also be understood that while the remote computing device 104a in FIG. 2 is illustrated as a single device, this is also merely an example. In some embodiments, the detection logic 144a the control logic 144b, may reside on different devices.

FIG. 3 depicts an interface 300 for viewing data regarding the vehicle 102, according to embodiments disclosed herein. While in some embodiments, the interface 300 may be provided by the computing infrastructure 128 and/or remote computing device 104a to the administrator computing device 104b. As illustrated, the interface 300 includes a view status data option 330, a view location data option 332, an add new vehicle option 334, and a remove vehicle option 336. As discussed in more detail below, in response to selection of the view status data option 330, remote computing device 104a can provide one or more interfaces for viewing current status of one or more vehicles (such as to the administrator computing device 104b). Similarly, selection of the view location data option 332 can cause the remote computing device 104a to provide one or more interfaces regarding the locations of the one or more vehicles. Selection of the add new vehicle option 334 and/or the remove vehicle option 336 causes the remote computing device 104a to add a vehicle and/or remove a vehicle from the monitoring and/or control.

It should be understood that while in some embodiments, a vehicle may be added or removed in response to selection of the options 334 and 336, respectively, this is merely an example. In some embodiments, vehicles may be added or removed automatically, based on whether the corresponding computing infrastructures 128 are in communication with the remote computing device 104a. As an example, if a new computing infrastructure on vehicle is detected and authenticated, this vehicle can be automatically added and provided in the interface 300. Similarly, in some embodiments, the vehicle may be authenticated by the computing infrastructure 128 sending a vehicle identifier to the remote computing device 104a. The remote computing device 104a may then determine whether monitoring of the vehicle is permissible.

Figure 4:
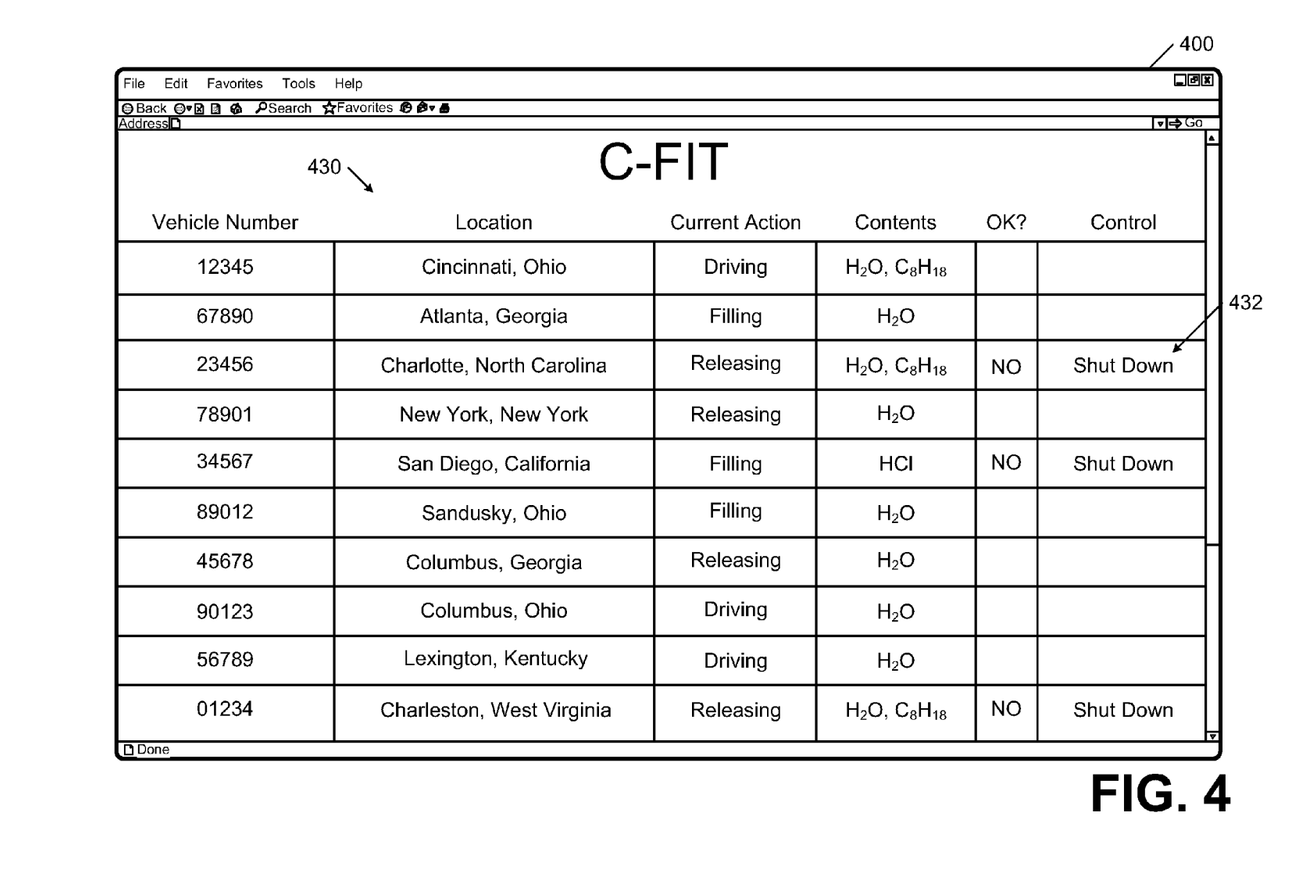
FIG. 4 depicts an interface for providing location and contents data for a plurality of vehicles, according to embodiments disclosed herein.

FIG. 4 depicts an interface 400 for providing location and contents data for a plurality of vehicles, according to embodiments disclosed herein. As illustrated, in response to selection of the view status data option 330, the interface 400 may be provided and may include a chart 430 that provides information regarding a one or more vehicles. More specifically, the current location, current action, and current contents may be provided. Additionally, an indication regarding whether the current action at the current location and with the current contents is acceptable. If not, a control option 432 may be provided to the administrator.

As an example, vehicle number 23456 is currently located in Charlotte, N.C. and is currently in the process of discharging a fluid that includes water ($H_2O$) and hydrocarbons ($C_8H_{18}$). Additionally, the computing infrastructure 128 and/or the remote computing device 104a have determined that this is not an acceptable action and provides the control option 432 to the administrator (in this case an option to shut the vehicle and/or pump engagement down). This determination can be made first by determining governmental (or other) regulations for releasing certain chemicals in predetermined geographic areas. Once the vehicle has entered one of the predetermined geographic areas, the computing infrastructure 128 and/or remote computing device 104a can determine whether the fluid in the vehicle violates any of the regulations. If so, preventative measures may be implemented, such as automatic shutdown, and/or a user option for shutdown, as illustrated in FIG. 4, etc.

Additionally, by selecting one of the locations listed in the interface 400, additional information may be sent, such as that illustrated in FIG. 5, described below. Similarly, by selection of one of the actions listed under the current action column, the remote computing device 104a can provide an interface regarding the progress of that current action. By selection of one of the items listed under the contents tab, a more complete identification of the fluid in that vehicle may be provided. By selection of an item in the OK column, the regulation may be provided, as well as a reason that the regulation was violated and/or not violated. Selection of an item in the control column provides causes that control operation to be performed.

Figure 5:
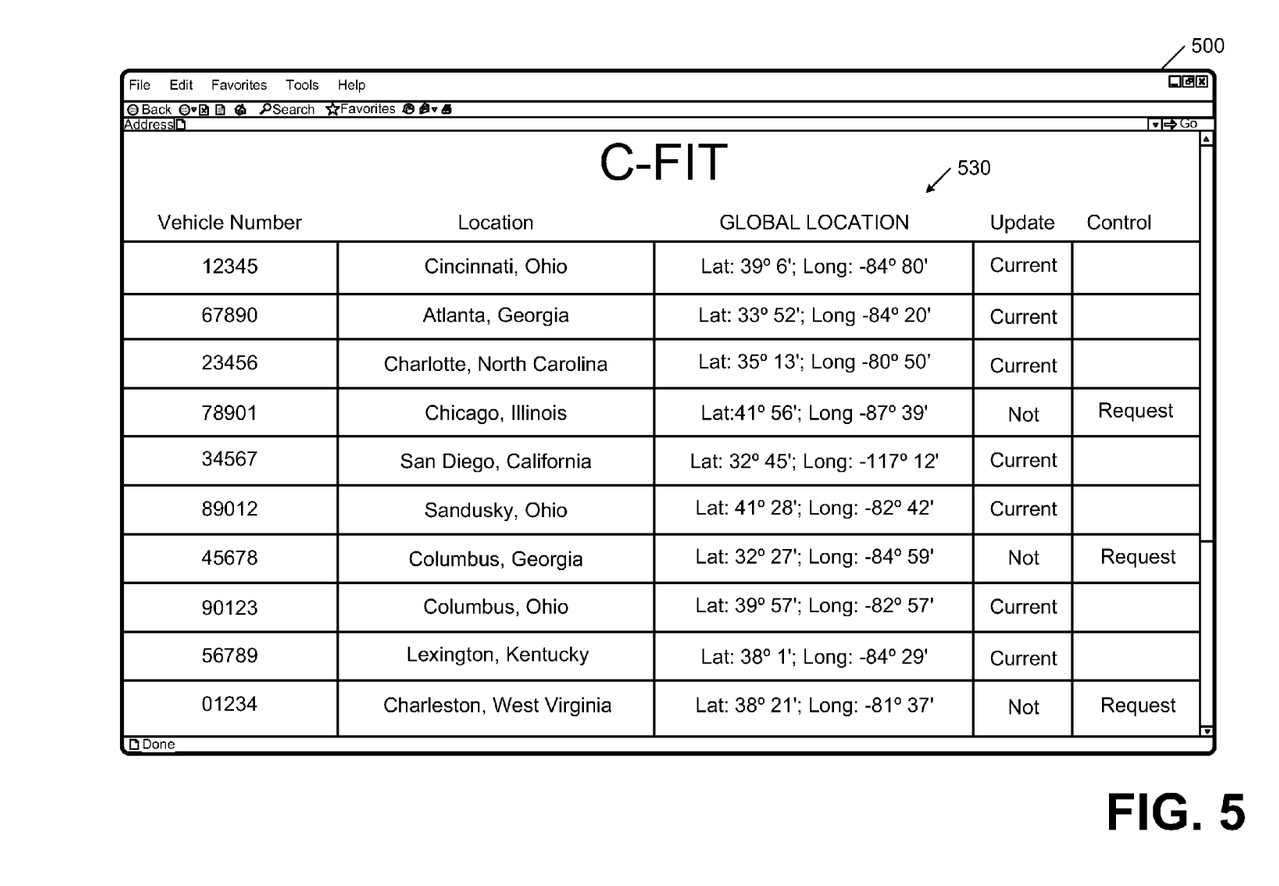
FIG. 5 depicts an interface for providing global location data regarding a plurality of vehicles, according to embodiments disclosed herein.

FIG. 5 depicts an interface 500 for providing global location data regarding a plurality of vehicles, according to embodiments disclosed herein. As illustrated, in response to selection of the view location data option 332 (FIG. 3), the interface 500 may be provided. The interface 500 provides a chart 530 that includes a location column, similar to the location column in the chart 430 from FIG. 4. Also included is a global location column, which provides an exact current location of the vehicle (more specific than in chart 430 from FIG. 4). An update column is also included and indicates whether the listed location data and/or global location data are current. If not, a user option may be provided for requesting the current location data.

It should be understood that while the embodiment of FIG. 5 illustrates that the location data may be out of date, this is merely an example. More specifically, in some embodiments, the location (and other data provided in the interfaces from FIGS. 4, 5, and 6) is automatically and/or consistently updated. Consequently, in such embodiments, the control column in FIG. 5 may include the control option 432 and/or other action options, similar to those depicted in FIG. 4.

Similarly, it should be understood that the global location data may be determined from a plurality of sources. More specifically, while some of the data may be retrieved from the locator data 238b and/or vehicle data 238a, which are stored in the data storage 236, at least a portion of the data provided in the interface 500 may be determined via execution of the detection logic 144a and/or control logic 144b.

Figure 6:
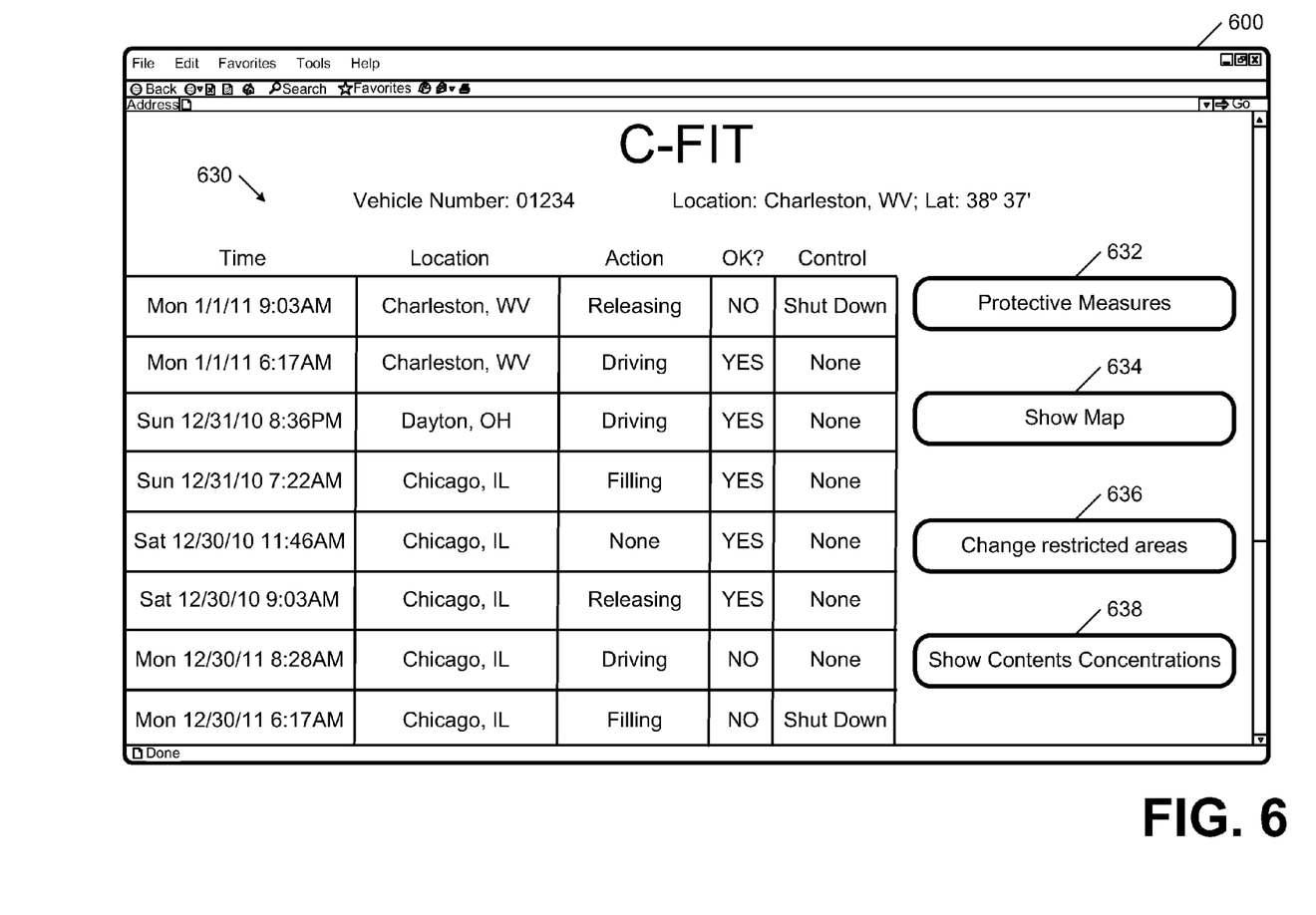
FIG. 6 depicts an interface for providing historical data regarding a vehicle, according to embodiments disclosed herein.

FIG. 6 depicts an interface 600 for providing historical data regarding a selected vehicle, according to embodiments disclosed herein. As illustrated, in response to selection of vehicle number 01234 from FIGS. 4 and/or 5, the interface 600 may be provided. The interface 600 may provide a chart 630 that includes one or more entries indicating location data and other data at specific times for a particular vehicle. As illustrated, on Dec. 30, 2010 at 9:03 AM, vehicle 01234 was in Chicago, Ill. During that time, vehicle 01234 was receiving a fluid. As this activity was unacceptable for that location, a shutdown instruction was implemented. Similar activities are also provided in the chart 630.

Also included in the interface 600 are a protective measures option 632, a show map option 634, a change restricted areas 636, and a show contents concentrations option 638. The protective measures option 632 may be configured to provide different measures in response to a vehicle performing a restricted activity. While shutting down the system is illustrated in FIGS. 4-6 as a protective measure, other protective measures may be implemented, such as reporting the activity to the authorities, reporting the activity to the owner of the property, requesting the vehicle driver to immediately report to a predetermined location, etc. Additionally, the show map option 634 can provide a graphical depiction of the information in the chart 630. The change restricted areas option 636 may be configured to provide an option for the administrator or other entity to change the restriction criteria for various geographical locations. As an example, if a certain piece of property is subject to a change in zoning or other condition, the restricted materials may also change. Accordingly, an option may be provided to implement this change. Additionally, the show contents concentrations option 638 may be configured to provide the ingredients and concentrations of the vehicle contents at the various times illustrated in chart 630.

Additionally, while not explicitly illustrated in FIGS. 3-6, some embodiments may be configured to provide a user interface that illustrates a graphical representation of a route that one or more of the monitored vehicles have taken. The user interface may illustrate receiving and/or discharging of fluid, the type of fluid, and/or whether the receipt and/or discharger are allowable. Other features may also be provided.

Figure 7:
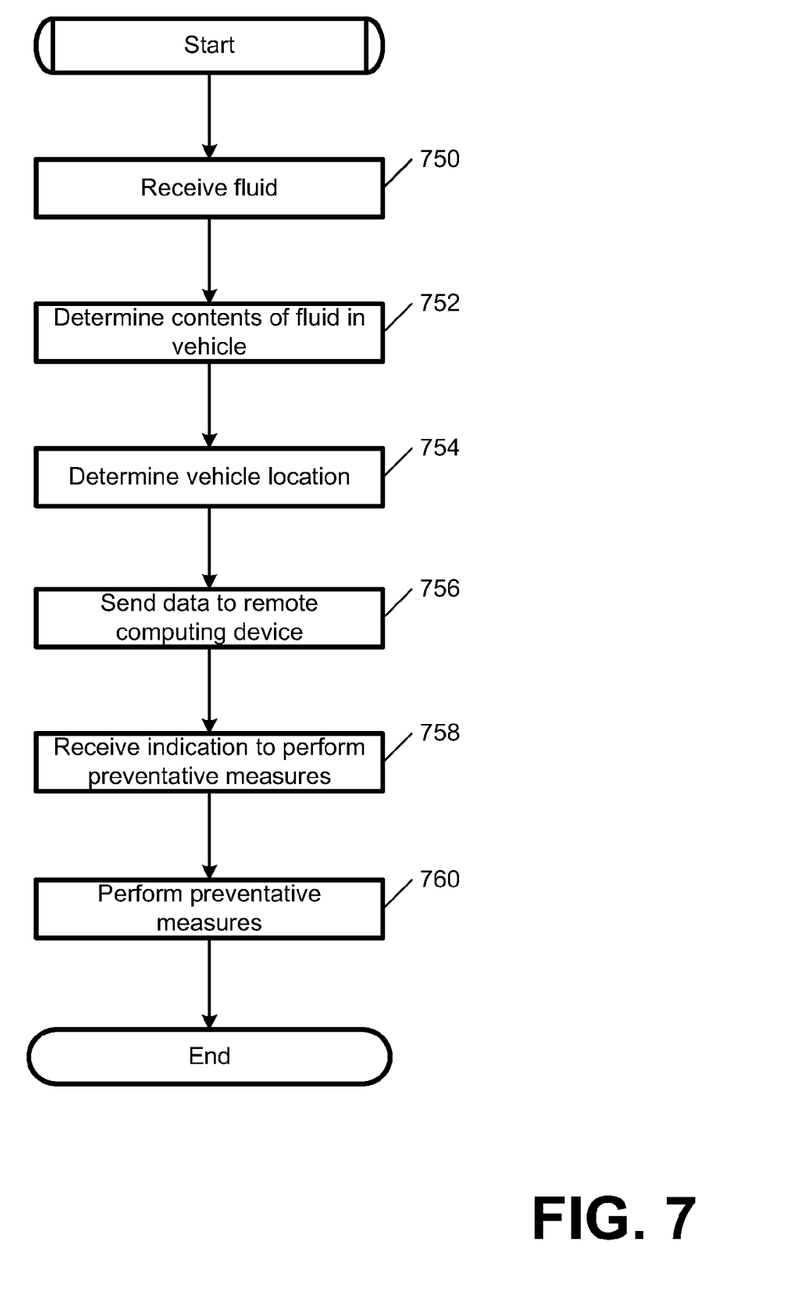
FIG. 7 depicts a process for a vehicle to determine location and contents data during fluid intake, according to embodiments disclosed herein.

FIG. 7 depicts a process for a vehicle to determine location and contents data during intake of a fluid, according to embodiments disclosed herein. At block 750, the vehicle 102 can receive the fluid. At block 752, a determination may be made regarding the specific ingredients and concentrations of the fluid in the vehicle 102. At block 754, a determination of vehicle location may be made. At block 756, the accumulated data from blocks 750-754 may be sent to the remote computing device 104a. At block 758, an indication may be received regarding an indication to perform a preventative measure such as shutting down the pump engagement 124 and/or other flow mechanism. At block 760, the preventative measure may be performed.

Figure 8:
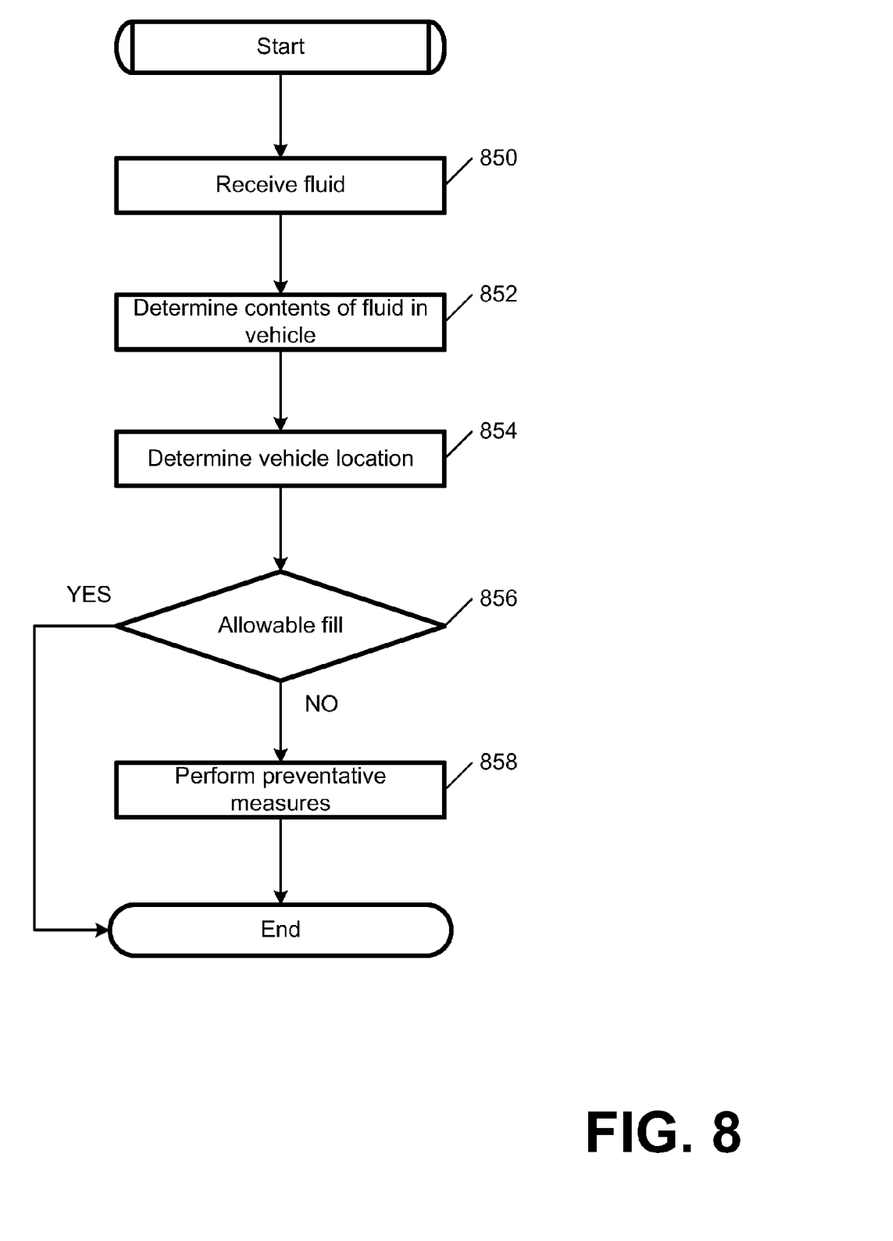
FIG. 8 depicts a process for a remote computing device to determine location and contents data of a vehicle during fluid intake, according to embodiments disclosed herein.

FIG. 8 depicts a process for the remote computing device 104a to determine location and contents data of a vehicle during intake of a fluid, according to embodiments disclosed herein. As illustrated in block 850, the fluid may be received at the vehicle 102. At block 852, a determination may be made regarding the ingredients and concentrations of the fluid in the vehicle 102. At block 854, a determination may be made regarding the vehicle location. At block 856, a determination may be made regarding whether an allowable fill is being performed. If not, at block 858, preventative measures may be performed. If an allowable fill is being performed, the process may end.

Figure 9:
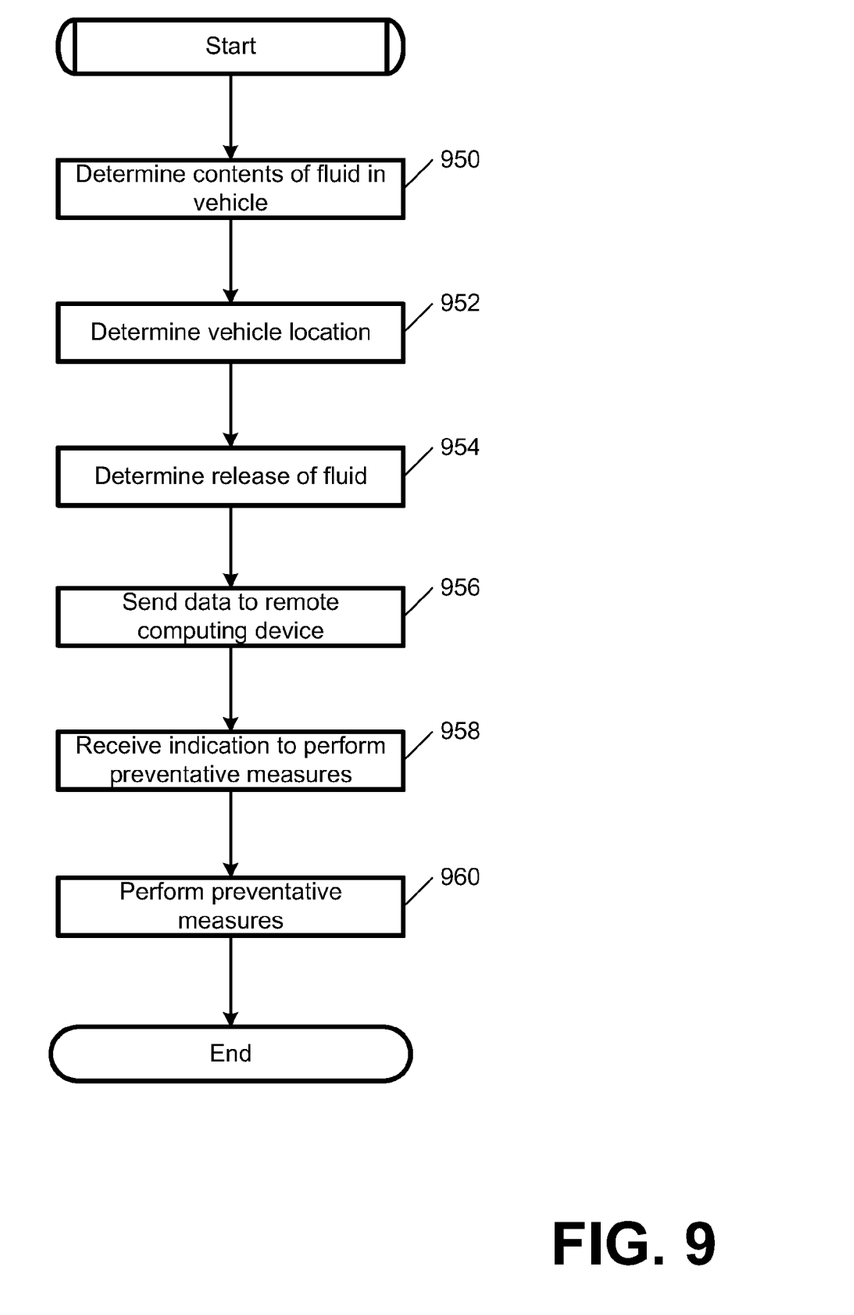
FIG. 9 depicts a process for a vehicle to determine location and contents data during fluid discharge, according to embodiments disclosed herein.

FIG. 9 depicts a process for a vehicle to determine location and contents data during release of a fluid, according to embodiments disclosed herein. As illustrated at block 950, a determination may be made regarding contents in the vehicle 102. At block 952, a determination may be made regarding a vehicle location. At block 954, a determination may be made regarding whether the vehicle 102 is releasing the fluid. At block 956, the acquired data from blocks 950-954 may be sent to the remote computing device 104a. At block 958, an indication may be received to perform preventative measures. At block 960, the preventative measures may be performed.

Figure 10:
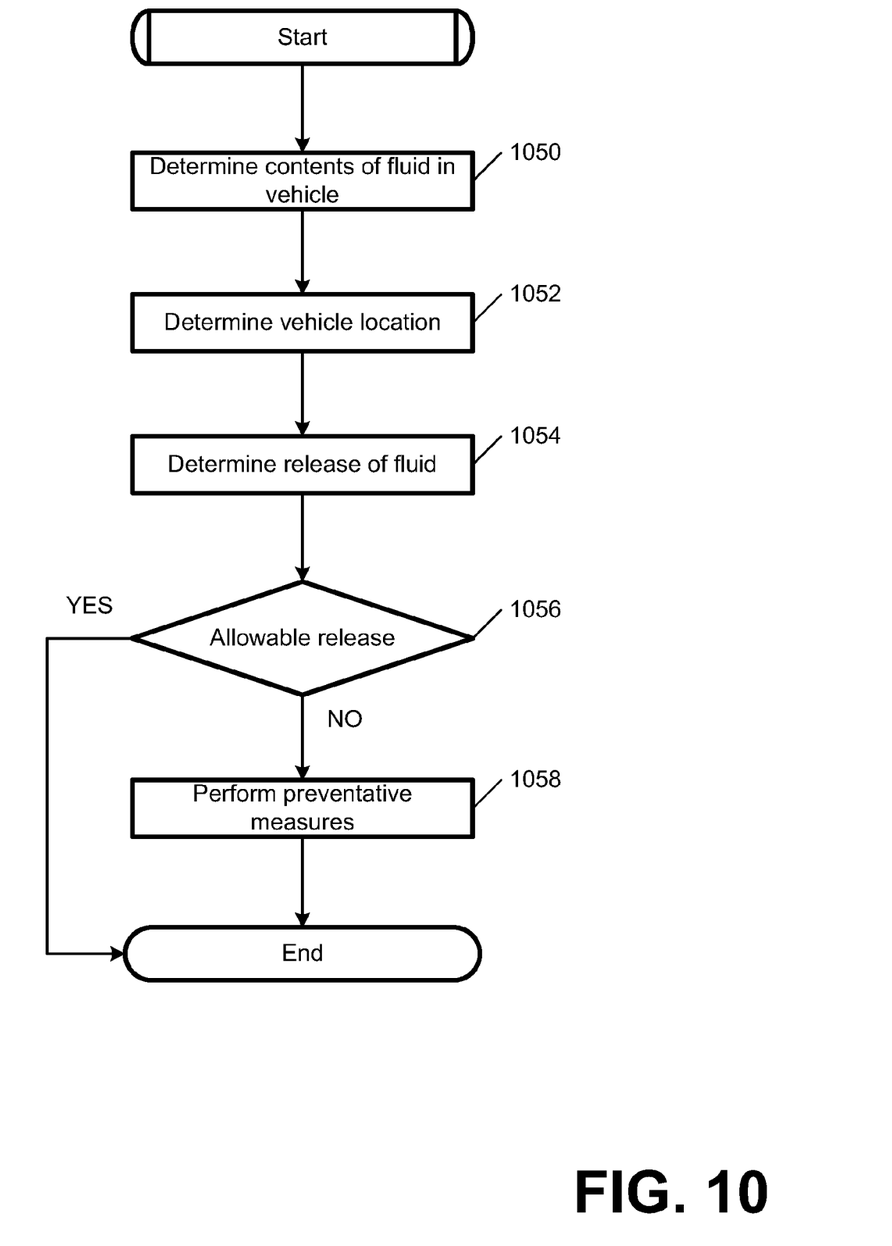
FIG. 10 depicts a process for a remote computing device to determine location and contents data of a vehicle during release, according to embodiments disclosed herein.

FIG. 10 depicts a process for the remote computing device 104a to determine location and contents data of a vehicle during release of a fluid, according to embodiments disclosed herein. As illustrated in block 1050, the fluid contents (e.g., ingredients, concentration, etc.) may be determined. At block 1052, the vehicle location may be determined. At block 1054 a determination regarding whether the fluid has been discharged. At block 1056, a determination may be made regarding whether the discharge is allowable. If not at block 1058, preventative measures may be performed. If the release is allowable, the process may end.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

What is claimed is:

1. A method for fluid identification and tracking, comprising:
   determining that a vehicle is receiving a fluid by means of a mechanism that controls, measures and reports receipt of fluids;
   determining an ingredient of the fluid;
   determining a vehicle location;
   determining by a computing device, based on the ingredient and the vehicle location, whether receipt of the fluid is allowable;
   in response to determining that receipt of the fluid at the vehicle location is not allowable, performing, by a computing device, a preventative measure comprising controlling the mechanism that controls, measures and reports receipt of fluids so that no further fluids may be received by the vehicle at the location;
   in response to determining that receipt of the fluid at the vehicle location is allowable:
      determining a subsequent vehicle location;
      determining that the vehicle is discharging at least a portion of the fluid by means of a mechanism that controls, measures and reports discharge of fluids;
      determining by a computing device, based on the ingredient and the subsequent location of the vehicle, whether discharging the fluid is allowable; and
      in response to determining that discharging the fluid at the subsequent location of the vehicle is not allowable, performing, by a computing device, a subsequent preventative measure comprising controlling the mechanism that controls discharge of fluids so that no further fluids may be discharged from the vehicle at the location.

2. The method of claim 1, further comprising providing an interface that includes data related to at least the following: the vehicle location, the subsequent vehicle location, the ingredient, the first preventative measure, and the subsequent preventative measure.

3. The method of claim 1, wherein determining the ingredient includes utilizing a density analysis on the fluid.

4. The method of claim 1, further comprising receiving information regarding allowability of the fluid discharged at a geographic location.

5. A non-transitory computer-readable medium for fluid identification and tracking that includes a program that, when executed by a computing device, causes the computing device to perform at least the following:
   determine that a vehicle is storing a fluid;
   determine an ingredient of the fluid;
   determine a vehicle location;
   determine, based on the ingredient and the vehicle location, whether discharging the fluid at the vehicle location is allowable;
   in response to determining that discharging the fluid at the vehicle location is allowable, sending a signal to control a mechanism that controls discharge of fluids so that fluids may be discharged from the vehicle at the location;
   in response to determining that receipt of the fluid at the vehicle location is allowable:
      determine a subsequent vehicle location;
      determine whether receiving fluid at the subsequent location of the vehicle is allowable; and
      in response to determining that receiving the fluid at the subsequent location of the vehicle is allowable, sending a signal to control a mechanism that controls receipt of fluids on the vehicle so that fluids may be received by the vehicle at the location.

6. The non-transitory computer-readable medium of claim 5, further comprising providing an interface that includes data related to at least the following: the vehicle location, the subsequent vehicle location, the ingredient, the first preventative measure, and the subsequent preventative measure.

7. The non-transitory computer-readable medium of claim 5, wherein determining the ingredient includes utilizing a density analysis on the fluid.

8. The non-transitory computer-readable medium of claim 5, wherein the program further causes the computing device to receive information regarding allowability of the fluid received at a geographic location.

9. The non-transitory computer-readable medium of claim 5, wherein the computing device is located at one of the following locations: at the vehicle and remote from the vehicle.

10. A system for fluid identification and tracking comprising:
   a computing device that includes a memory component that stores logic that causes the computing device to perform at least the following:
      determine that a vehicle is discharging a fluid by means of a mechanism that controls discharge of fluids;
      determine an ingredient of the fluid;
      determine a vehicle location;
      determine, based on the ingredient and the vehicle location, whether discharging of the fluid at the vehicle location is allowable;
      in response to determining that receipt of the fluid at the vehicle location is not allowable, perform a preventative measure comprising controlling the mechanism that controls discharge of fluids so that no further fluids may be discharged from the vehicle at the location;
      in response to determining that receipt of the fluid at the vehicle location is allowable:
         determine a subsequent vehicle location;
         determine that the vehicle is receiving at least a portion of the fluid by means of a mechanism that controls receipt of fluids;
         determine, based on the ingredient and the subsequent location of the vehicle, whether receiving the fluid at the subsequent location of the vehicle is allowable; and
         in response to determining that receiving the fluid at the subsequent location of the vehicle is not allowable, perform a subsequent preventative measure comprising controlling the mechanism that controls receipt of fluids so that no further fluids may be received by the vehicle at the location.

11. The system of claim 10, wherein the logic further causes the computing device to provide an interface that provides data related to at least the following: the vehicle location, the subsequent vehicle location, the ingredient, the first preventative measure, and the subsequent preventative measure.

12. The system of claim 10, wherein determining the ingredient includes utilizing a density analysis on the fluid and wherein the logic further causes the computing device to receive information regarding allowability of the fluid discharged at a geographic location.

13. The system of claim 10, further comprising:
   a pump engagement that facilitates intake and release of the fluid; and
   a flow meter that monitors volume and density of the fluid.

14. The system of claim 10, wherein the computing device is located at one of the following locations: at the vehicle and remote from the vehicle.

* * * * *